(12) United States Patent
Dunham et al.

(10) Patent No.: US 8,124,034 B2
(45) Date of Patent: Feb. 28, 2012

(54) ALKYLATION UNIT AND METHOD OF MODIFYING

(75) Inventors: Daryl Dunham, Ponca City, OK (US); Dale James Shields, Grayslake, IL (US)

(73) Assignee: UOP LLC, Des Plaines, IL (US)

( * ) Notice: Subject to any disclaimer, the term of this patent is extended or adjusted under 35 U.S.C. 154(b) by 293 days.

(21) Appl. No.: 12/490,549

(22) Filed: Jun. 24, 2009

(65) Prior Publication Data

US 2010/0329945 A1 Dec. 30, 2010

(51) Int. Cl.
*B01J 8/04* (2006.01)

(52) U.S. Cl. ........ 422/630; 422/608; 422/620; 422/631; 585/301; 585/716; 585/718; 585/719; 585/721; 585/722; 585/723

(58) Field of Classification Search .................. 422/608, 422/620, 630, 631; 585/716, 719, 718, 721, 585/722, 723, 301
See application file for complete search history.

(56) References Cited

U.S. PATENT DOCUMENTS

| | | | | |
|---|---|---|---|---|
| 2,615,928 A | | 10/1952 | Jolly | |
| 3,158,661 A | * | 11/1964 | Plaster et al. | 585/301 |
| 3,433,846 A | * | 3/1969 | Sweeney et al. | 585/311 |
| 3,544,651 A | * | 12/1970 | Chapman | 585/301 |
| 3,683,041 A | * | 8/1972 | Goldsby | 585/311 |
| 3,742,081 A | * | 6/1973 | Goldsby | 585/301 |
| 3,763,266 A | * | 10/1973 | Anderson | 585/301 |
| 3,787,518 A | * | 1/1974 | Henderson | 585/716 |
| 3,911,043 A | * | 10/1975 | Anderson | 585/716 |
| 4,046,516 A | * | 9/1977 | Burton et al. | 422/608 |
| 4,225,737 A | * | 9/1980 | Mikulicz et al. | 585/449 |
| 4,239,931 A | * | 12/1980 | Mikulicz | 585/723 |
| 4,275,032 A | * | 6/1981 | Anderson | 422/110 |
| 4,783,567 A | | 11/1988 | Kocal | |
| 4,863,697 A | | 9/1989 | Hann et al. | |
| 5,098,668 A | * | 3/1992 | Callen et al. | 422/111 |
| 5,114,675 A | | 5/1992 | Greco et al. | |
| 5,185,469 A | | 2/1993 | Lindley et al. | |
| 5,209,907 A | | 5/1993 | Hovis | |
| 5,258,568 A | | 11/1993 | Child et al. | |
| 5,277,881 A | * | 1/1994 | Partridge et al. | 422/241 |
| 5,407,830 A | | 4/1995 | Altman et al. | |
| 5,583,049 A | | 12/1996 | Altman et al. | |
| 5,639,930 A | * | 6/1997 | Penick | 585/722 |
| 5,789,640 A | | 8/1998 | Jin et al. | |
| 6,172,274 B1 | | 1/2001 | Gosling | |
| 6,187,986 B1 | | 2/2001 | Schlaeppi | |

OTHER PUBLICATIONS

Hewson, HF Alkylation, The Oil and Gas Journal, Mar. 22, 1954, vol. 52, No. 46, pp. 189, 192-193, 195-199, 202.
Shanley et al., Numerous Improvements in HF Alkylation Will Cut Costs and Reduce Losses, The Oil and Gas Journal, Dec. 1, 1945, vol. 44, No. 30, pp. 94-96, 98. Stewart et al., Design Concepts for a Hydrogen Fluoride Emergency De-Inventory System, Process Safety Progress, Apr. 1994, vol. 13, No. 2, pp. 105-107.
Thornton, JR., Three Unusual Features in New HF Alkylation Unit, Petroleum Processing, Oct. 1954, vol. 9, No. 10, pp. 1570-1573.

\* cited by examiner

*Primary Examiner* — Walter D Griffin
*Assistant Examiner* — Huy-Tram Nguyen
(74) *Attorney, Agent, or Firm* — James C Paschall

(57) ABSTRACT

One exemplary embodiment can be a method of modifying an alkylation unit to increase capacity. The method may include combining a first alkylation zone with a second alkylation zone. Generally, the first alkylation zone includes a first settler having a height and a width. Typically, the width is greater than the height. In addition, the second alkylation zone may have a second settler having a height and a width. Usually, the height is greater than the width.

13 Claims, 1 Drawing Sheet

FIG. 1

ALKYLATION UNIT AND METHOD OF MODIFYING

FIELD OF THE INVENTION

This invention generally relates to an alkylation unit, particularly to an alkylation unit using an acid catalyst.

DESCRIPTION OF THE RELATED ART

Generally, alkylation is a process that can be used to produce a high quality, high octane gasoline from lower boiling feeds. Usually, commercial refinery plants alkylate a feed including an isoparaffin stream, typically including isobutane, and an olefin stream, typically including one or more C3-C4 olefins, to form branch chain paraffin products boiling in the gasoline range, which can include hydrocarbons boiling up to about 200° C.

Increasing capacity of an alkylation unit may be implemented by adding a second stage reactor and settler. This addition can make efficient use of the existing fractionation equipment and the isoparaffin recycle stream. However, such a modification can double the alkylation catalyst inventory. In a gravity-fed alkylation system, a settler can provide an alkylation catalyst via gravity at a lower operating pressure. However, such a system uses more alkylation catalyst as compared to other systems. Although doubling the acid inventory can obtain a corresponding increase of about 25-about 50%, by weight, in alkylation capacity, the alkylation catalyst may be an acid that can create health, safety, and environmental concerns.

Therefore, minimizing the amount of acid in inventory can be desired. The inventory of the acid catalyst in the process and the number of locations of parts joined by flanges or moving parts, such as pump seals, can create risk of acid escaping from the process. Reducing the amount of acid inventory and the handling of acid by pumps are desirable to improve safety and minimize containment failures.

SUMMARY OF THE INVENTION

One exemplary embodiment can be a method of modifying an alkylation unit to increase capacity. The method may include combining a first alkylation zone with a second alkylation zone. Generally, the first alkylation zone includes a first settler having a height and a width. Typically, the width is greater than the height. In addition, the second alkylation zone may have a second settler having a height and a width. Usually, the height is greater than the width.

Another exemplary embodiment may be an acid alkylation unit. The acid alkylation unit can include a first alkylation zone and a second alkylation zone. The first alkylation zone can include a first settler having a height and a width. Usually, the width is greater than the height and adapted to receive an acid reaction alkylation effluent. The second alkylation zone may include a second settler having a height and a width. Usually, the height is greater than the width and adapted to receive another acid reaction alkylation effluent.

A further exemplary embodiment may be a method of modifying an acid alkylation unit to increase capacity. The method can include combining a first alkylation zone with a second alkylation zone. Generally, the first alkylation zone has a first settler providing an acid catalyst via a fluid transfer device to a first alkylation reactor. Typically, the second alkylation zone includes a second settler providing an acid catalyst via gravity to a second alkylation reactor.

The embodiments disclosed herein can provide an increase in an alkylation unit capacity by adding another reactor and settler in series to an existing reactor receiving an alkylation catalyst via gravity from a settler. However, the added unit can lower alkylation catalyst inventory by utilizing a settler and reactor arrangement providing separated acid from the settler by using a fluid transfer device. As such, the added equipment can lower acid inventory as compared to providing a reactor fed by an alkylation catalyst via gravity. Providing an alkylation catalyst via a fluid transfer device can operate at an acid:hydrocarbon volume ratio of about 1.1-about 2.5, as compared to providing an alkylation catalyst via gravity that typically operates at an acid:hydrocarbon volume ratio greater than about 2.5:1. Alternatively, a gravity-driven zone can be added to a fluid transfer zone to minimize the use of pumps, and also may have a lower overall acid inventory as compared to a system solely using gravity to transfer catalyst.

DEFINITIONS

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules. Additionally, characterizing a stream as, e.g., an "olefin stream" can mean a stream including or rich in at least one olefin.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 30%, preferably about 50%, and optimally about 70%, by mole, of a compound or class of compounds in a feed, an effluent, or a stream.

As used herein, the term "substantially" can mean an amount of at least generally about 80%, preferably about 90%, and optimally about 99%, by mole, of a compound or class of compounds in a feed, an effluent, or a stream.

As used herein, the term "vapor" can mean a gas or a dispersion that may include or consist of one or more hydrocarbons.

As used herein, the term "vaporization" can mean using at least one of heat and pressure to change at least a portion of a liquid to a gas optionally forming a dispersion, such as a gas entraining at least one of liquid and solid particles.

As used herein, the term "communicating" may mean two objects capable of receiving, directly or indirectly, a substance transmitted from one to the other.

As used herein, the term "hydrogen fluoride" can include at least one of a hydrogen fluoride or a hydrofluoric acid. Generally, a hydrofluoric acid is a solution of a hydrogen fluoride in water, where the hydrogen fluoride can disassociate and may form ions of $H_3O^+$, $H^+$, $FHF^-$, and $F^-$.

As depicted, process flow lines in the figures can be referred to as lines, pipes, spargers, feeds, effluents, or streams. Particularly, a line, a sparger, or a pipe can contain one or more feeds, effluents, or streams, and one or more feeds, effluents, and streams can be contained by a line, a sparger, or a pipe. Generally, a sparger is a pipe forming a plurality of holes to improve dispersing of material from inside the pipe.

BRIEF DESCRIPTION OF THE DRAWING

FIG. 1 is a schematic depiction of an exemplary acid alkylation unit or system.

DETAILED DESCRIPTION

Figure 1:
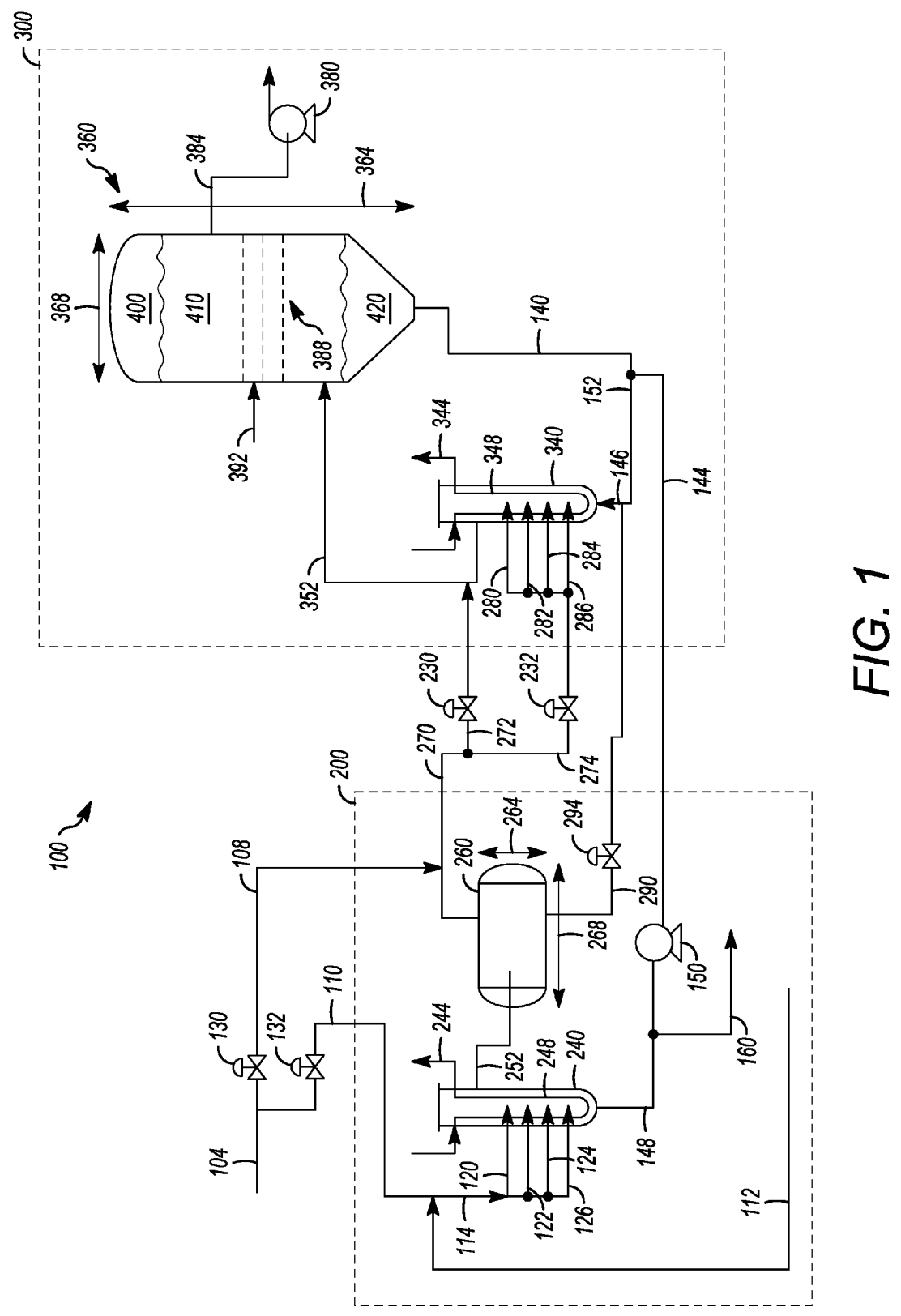

Referring to FIG. 1, an acid alkylation unit or system 100 can include a first alkylation zone 200 and a second alkylation zone 300, which may be arranged in parallel or series, preferably series. Typically, the zone 200 or the zone 300 can be in an existing unit or system 100. To increase production, the zone 200 or zone 300 can be added depending on the existing zones of the acid alkylation unit or system 100. Preferably, the zone 200 can be added to the zone 300. Some of the features and/or contents of at least one vessel are depicted schematically in a cross-sectional view.

Usually, the alkylation reaction can include the reaction of an isoparaffin, such as isobutane, with an olefin or other alkylating agent such as propylene, isobutylene, butene-1, butenes-2, and amylenes. Generally, the reaction of an isoparaffin with a C3 or a C4 olefin, such as isobutylene, butene-1, and/or butenes-2, is an example of a preferred reaction involving these specified materials and mixture. One preferred mixture is an isoparaffin and typically a mixed "butene" produced from a catalytic cracking operation, which can include about 25%, by volume, of butene-1, about 30%, by volume, of isobutylene and about 45%, by volume, of butenes-2. Usually, the stream rich in isobutane can at least be partially provided by recycling isobutane from a downstream fractionation zone and include make-up isobutane from refinery or chemical manufacturing units.

Typically, the alkylation catalyst can include hydrogen fluoride, a sulfuric acid, a hydrofluoric acid, a phosphoric acid, a metal halide, or other suitable alkylation catalyst. Preferably, the catalyst is a hydrofluoric acid. Generally, the alkylation reaction is carried out with substantial molar excess of isoparaffin:olefin, typically in excess of about 1:1, usually about 4:1-about 70:1, preferably about 5:1-about 20:1. Usually, the system or unit 100 can maintain an acid:hydrocarbon volume ratio of less than about 3:1, preferably less than about 2.5:1. As a consequence, the embodiments disclosed herein can obtain the benefits of a gravity-fed settler system with reduced acid inventories. Generally, the volume ratio of acid:hydrocarbon can be about 1:1-about 2.5:1. This volume can be less than what is typically required for gravity-driven units with riser-reactors that can operate with a volume ratio of acid:hydrocarbon of about 4:1. The gravity-driven system can operate at a lower pressure reducing the risk of leaks due to increased pressures. Thus, the catalyst inventory can be reduced without adding a pump for acid circulation. Moreover, employing a heat exchange in the reaction zone can reduce the amount of catalyst circulation normally required as a heat sink in a riser-reactor system.

The first alkylation zone 200 can include a first alkylation reactor 240, preferably a cooler-reactor 240, a first settler 260, and a fluid transfer device 150, such as a pump. Although a cooler-reactor 240 is disclosed, other reactors, such as a riser-reactor, can be utilized. Generally, the first cooler-reactor 240 can receive a cooling water stream 244 that is passed through one or more cooling coils 248. The first settler 260 can be generally cylindrical and can have a height 264 and a width 268. Typically, the width 268 is greater than the height 264. Usually, the height is the diameter of the first settler 260 and is less than the width 268. The first settler 260 can operate at a pressure up to about 1,500 kPa. Generally, the acid:hydrocarbon volume ratio in the first zone 200 can be about 1.1-about 2.5.

The second alkylation zone 300 can include a second alkylation reactor 340, such as a second cooler-reactor 340, a second settler 360, and a fluid transfer device 380, such as a pump, communicating with the second settler 360. Although a second alkylation reactor 340 is depicted as a cooler-reactor, it should be understood that any suitable alkylation reactor may be used. Typically, the second cooler-reactor 340 can receive a cooling water stream 344 passing through one or more cooling coils 348. The second settler 360 can have a height 364 and a width 368. Usually, the height 364 exceeds the width 368. Generally, the width 368 can be the diameter of the substantially cylindrical second settler 360. The second settler 360 can provide the alkylation catalyst to the cooler-reactor 340 via gravity. The second settler 360 can operate at a pressure of up to about 1,100 kPa, preferably about 800-about 1,100 kPa. Generally, the acid:hydrocarbon volume ratio in the second zone 300 can be no more than about 2.5:1.

The first and second cooler-reactors 240 and 340 can be carried out at pressures varying from about 100-about 7,000 kPa, preferably about 800-about 1,600 kPa with a residence time of about 20-about 300 seconds. The temperature of the reaction can vary but usually ranges from about −40-about 70° C. In the reaction of, e.g., an isoparaffin, such as isobutane with a C3 and/or a C4 olefin, the reaction temperature is preferably about 15-about 40° C.

The acid alkylation unit or system 100 can receive a stream 104 including one or more olefins. Typically, at least a portion 108 of the stream 104, including one or more olefins, may be bypassed around the first cooler-reactor 240. Typically, at least about 25-about 75%, by volume, optimally about 50%, by volume, of the stream 104 can be bypassed as the portion 108. The remainder can pass as a stream 110 to the first cooler-reactor 240. The control valves 130 and 132 can control the volume of the streams 108 and 110. A stream 112, including one or more isoparaffins, typically isobutane, can be combined with the stream 110. Usually, the stream 112, including one or more isoparaffins, can include isoparaffins obtained from other units, and a recycled stream from downstream fractionation units. The combined streams 110 and 112 can form a hydrocarbon feed 114. This hydrocarbon feed 114 can be split through several spargers, namely a sparger 120, a sparger 122, a sparger 124, and a sparger 126 before entering the cooler-reactor 240. Thus, the vertically spaced spargers 120, 122, 124, and 126 may ensure good dispersion of the hydrocarbons through an acid phase in the cooler-reactor 240.

The hydrocarbon feed 114 can enter the cooler-reactor 240 and form one or more alkylation products. An alkylation catalyst can enter the cooler-reactor 240 via a line 148 and react to provide a cooler-reactor effluent 252. The effluent 252 can enter the first settler 260. An acid phase can separate from a hydrocarbon phase and can exit via a line 290 and pass a valve 294, as hereinafter described. The hydrocarbon phase can exit via a line 270 and be split through lines 272 and 274. Particularly, control valves 230 and 232 can be used to bypass at least a portion of the reaction effluent, such as about 25-about 75%, by volume, optimally about 50% by volume, in a line 272 around the second cooler-reactor 340 while the remainder can be provided as a feed 274. The feed 274 can be split through several spargers, namely a sparger 280, a sparger 282, a sparger 284 and a sparger 286, before entering the cooler-reactor 340. Thus, the vertically spaced spargers 280, 282, 284, and 286 may ensure good dispersion of the hydrocarbons through the acid phase in the cooler-reactor 340. The alkylation catalyst can be provided to the cooler-reactor 340 through a line 146. The reactor effluent can pass through a line 352 to the second settler 360.

Alternatively, the line 352 can form a riser-reactor, which may have vertical and horizontal sections preferably with the same diameter. The bypass stream in the line 272 can act as a feed and optionally be provided through one or more spargers. The alkylation reaction can continue to an inlet of and provide a reaction product to the settler 360. Usually, the alkylation reaction occurs at a pressure of about 100-about 7,000 kPa, preferably about 400-about 1,600 kPa with a residence time of about 10-about 300 seconds. The temperature of the reaction can vary but usually ranges from about −40- about 70° C. In the reaction of, e.g., an isoparaffin, such as isobutane with a C3 and/or a C4 olefin, the reaction temperature is preferably about 15-about 40° C. In one exemplary embodiment, an existing gravity-fed alkylation riser-reactor can be modified with a cooler-reactor by, e.g., replacing a cooling water exchanger. Generally, cooling a feed with a cooling water exchanger requires a greater inventory of reactants to absorb the heat of the reaction as compared to cooling the reactants and products during the reaction with a cooler-reactor. Thus, the acid inventory may be lowered.

Generally, the second settler 360 can allow the second reactor effluent to split into three phases, namely, a vapor phase 400, a hydrocarbon phase 410, and an alkylation catalyst or acid phase 420. The hydrocarbon phase 410 can be drawn through a line 384, passed through the fluid transfer device 380, and provided to downstream fractionation units for recovering the alkylate product. The hydrocarbon phase 410 can surround one or more contacting trays 388 for lowering the fluoride content in the hydrocarbon phase 410 and minimize downstream treatment for removing fluorides from the hydrocarbons. The acid phase 420 can pass through a line 140 and be provided via a line 144 to the fluid transfer device 150 and through a line 152 to the second cooler-reactor 340. The acid phase in the line 290 can combine with the acid phase in the line 152, and the combination can flow to the second cooler-reactor 340 through the line 146. The acid phase in the line 144 can pass to the pump 150 and be supplied to the first cooler-reactor 240 with a slipstream in a line 160 being sent to a regeneration zone for regenerating the alkylation catalyst. The regenerated acid catalyst can be returned via a line 392 to the second settler 360, although the regenerated catalyst can be provided to other locations within the system 100, such as at least one of the feed streams 114 and 274.

Any suitable control scheme may be utilized for, e.g., bypassing a portion of one or more streams around the cooler-reactors 240 and 340. One or more exemplary settlers, alkylation reactors, fractionation zones, and catalyst regeneration zones, are disclosed in, e.g., U.S. Pat. No. 5,098,668. The embodiments disclosed herein can be used in a new alkylation unit or modify an existing alkylation unit.

Generally, the embodiments provided herein can provide a method of expanding capacity of an alkylation unit, such as a hydrogen fluoride alkylation unit, by adding a pumped acid circulation zone 200 to an existing gravity-driven acid circulation zone 300. Adding such a pumped system can reduce the inventory as compared to adding another gravity-driven zone. Alternatively, the benefit of adding a second zone 300 to a first zone 200 may be operating at a lower pressure. Moreover, the first zone 200 can be isolated while operating the second zone 300 during, for example, maintenance shutdowns.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method of modifying an acid alkylation unit to increase capacity, comprising:
   A) combining a first alkylation zone with a second alkylation zone wherein:
      1) the second alkylation zone comprises a second settler providing an acid catalyst via a fluid transfer device to a first alkylation reactor; and
      2) the second alkylation zone comprises a second settler providing an acid catalyst via gravity to a second alkylation reactor.

2. The method according to claim 1, wherein the first alkylation zone further comprises a first cooler-reactor communicating with the first settler wherein the first settler receives a reactor effluent from the first cooler-reactor.

3. The method according to claim 2, wherein the second alkylation zone further comprises a second cooler-reactor communicating with the second settler wherein the second settler receives the reactor effluent from the second cooler-reactor.

4. The method according to claim 1, wherein the first alkylation zone is added to the second alkylation zone during modification.

5. The method according to claim 3, wherein a fluid transfer device provides a stream comprising an alkylation catalyst to the first cooler-reactor.

6. The method according to claim 5, wherein an alkylation catalyst is provided to the second cooler-reactor via gravity.

7. The method according to claim 3, wherein the first and second cooler-reactors receive a hydrocarbon feed comprising one or more olefins and one or more isoparaffins.

8. The method according to claim 7, wherein the one or more olefins are comprised in a stream, wherein at least a portion of the olefin stream is bypassed around the first cooler-reactor.

9. The method according to claim 8, wherein about 25-about 75%, by volume, of the olefin stream is bypassed around the first cooler-reactor.

10. The method according to claim 3, wherein the first and second cooler-reactors receive an alkylation catalyst and a hydrocarbon feed.

11. The method according to claim 10, wherein a volume ratio of the alkylation catalyst and hydrocarbon feed is about 1:1-about 2.5:1.

12. The method according to claim 7, wherein at least a portion of the one or more isoparaffins is provided by a recycle stream.

13. The method according to claim 3, wherein the second alkylation zone further comprises a riser-reactor receiving an effluent from the second cooler-reactor and providing a reaction product to the second settler.

* * * * *